United States Patent
Baek et al.

(10) Patent No.: US 6,979,737 B1
(45) Date of Patent: Dec. 27, 2005

(54) QUINOXALINE-CONTAINING AB$_2$ MONOMER FOR HYPERBRANCHED AROMATIC POLY(ETHER-KETONES)

(75) Inventors: Jong-Beom Baek, Cheongju (KR); Loon-Seng Tan, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 270 days.

(21) Appl. No.: 10/695,730

(22) Filed: Oct. 23, 2003

Related U.S. Application Data

(60) Provisional application No. 60/453,333, filed on Feb. 28, 2003.

(51) Int. Cl.$^7$ .......................................... C07D 241/36
(52) U.S. Cl. ........................................ 544/355
(58) Field of Search ........................ 544/355

(56) References Cited

U.S. PATENT DOCUMENTS 6,552,195 B1 *  4/2003  Baek et al. ................ 544/353

OTHER PUBLICATIONS

Baek et al, "Synthesis and Polymerization of a bis(O-aminophenol)-Carboxylic Acid AB2 Monomer" Polymer Preprints, vol. 42(2), pp. 502-503 (2001), as abstracted by CAPLUS.*

Jong-Beom Baek, Loon-Seng Tan, Improved syntheses of poly(oxy-1,3-phenylencarbonyl-1,4-phenylene) and related poly(ether-ketones) using polyphosphoric acid/P2O5 as polymerization medium, Polymer, 44 (2003) 4135-4147, published Jul. 2003.

Jong-Beom Baek, Loon-Seng Tan, Synthesis of Hyperbranched Poly(Ether-Ketone) Containing Quinoxaline Moiety from an AB$_2$ Monomer in Polyphosphoric Acid/P$_2$O$_5$, *Polymer Preprints*, 2002, 43(1), 4-515, published in Mar. 2002.

* cited by examiner

*Primary Examiner*—James O. Wilson
*Assistant Examiner*—Zachary C. Tucker
(74) *Attorney, Agent, or Firm*—AFMCLO/JAZ; Charles E. Bricker

(57) ABSTRACT

A novel AB$_2$ monomer, 2,3-bis(4-phenyloxyphenyl)-6-quinoxaline carboxylic acid.

1 Claim, No Drawings

QUINOXALINE-CONTAINING AB$_2$ MONOMER FOR HYPERBRANCHED AROMATIC POLY(ETHER-KETONES)

CROSS REFERENCE TO RELATED APPLICATION

This application claims priority of the filing date of Provisional Application Ser. No. 60/453,333, filed Feb. 28, 2003.

RIGHTS OF THE GOVERNMENT

The invention described herein may be manufactured and used by or for the Government of the United States for all governmental purposes without the payment of any royalty.

BACKGROUND OF THE INVENTION

The present invention relates to a new quinoxaline-containing AB$_2$ monomer that is useful for the preparation of hyperbranched poly(ether-ketones).

Dendritic macromolecules such as dendrimers and hyperbranched polymers are a new class of highly branched polymers that have distinctly different properties from their linear analogs. Both dendrimers and hyperbranched polymers have much lower solution and melt viscosities than their linear analogs of similar molecular weights. They also have a large number of chain-ends whose collective influence dictates their overall physical and/or chemical behaviors. These features are attractive in terms of processability and offering flexibility in engineering required properties for specific applications. However, there is a practical advantage that hyperbranched polymers have over dendrimers at "raw material" level. Although dendrimers have precisely controlled structures (designated as generations), their preparations generally involve tedious, multi-step sequences that are impractical and costly in scale-up production. Synthesis of a hyperbranched polymer, on the other hand, is a one-pot process. Large quantities of hyperbranched polymers can be easily produced from AB$_x$(x≧2) monomers.

Because of their excellent thermal and mechanical properties, as well as their optical and electronic characteristics, aromatic, fused heterocyclic polymers such as polyquinoxalines and polybenzoxazoles continue to attract considerable attention. However, they have limited processability due to the nature of fused ring systems. Their insolubility and their softening temperatures are generally above their degradation temperatures. Chemical modification on the these materials, for example, by the use of solubilizing pendants or flexible units in the main chain, has been successful to improve their processability, allowing the optimization of their properties as a function of processability. Another viable approach to achieving this objective is to incorporate the elements of local rigidity and global randomness into the macromolecular architecture. Local rigidity provides the thermal, electronic and optical characteristics of the aromatic fused systems while global randomness frustrates entanglement of the polymer chains, leading to greater solubility. Dendritic structures clearly embody these qualities. However, as noted previously, hyperbranched structures have greater synthetic practicality.

Accordingly, it is an object of the present invention to provide a novel quinoxaline-containing AB$_2$ monomer that is useful for the preparation of hyperbranched poly(ether-ketones).

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided a novel AB$_2$ monomer, 2,3-bis(4-phenyloxyphenyl)-6-quinoxaline carboxylic acid, having the formula:

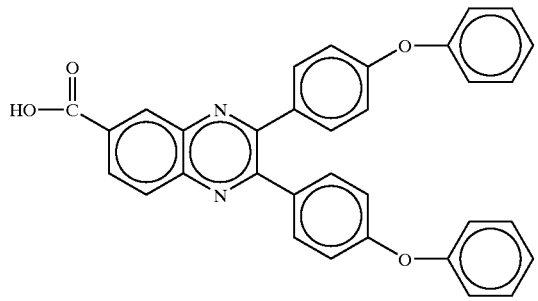

The AB$_2$ monomer, 2,3-bis(4-phenyloxyphenyl)-6-quinoxaline carboxylic acid, is synthesized as set forth in the examples which follow.

The AB$_2$ monomer, 2,3-bis(4-phenyloxyphenyl)-6-quinoxaline carboxylic acid, is useful for preparing the hyperbranched ether-ketone polymer:

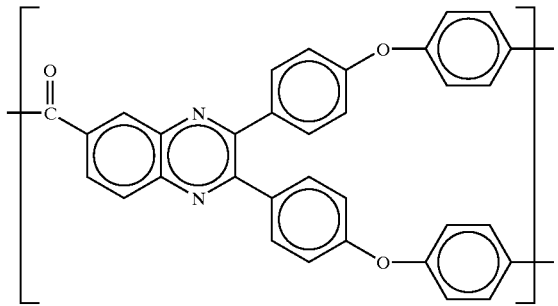

The following examples illustrate the invention:

EXAMPLE 1

1-(2-Methyl-3-butyn-2-ol)-2-(4-phenyloxyphenyl) ethyne

Into a 1 L three-necked, round-bottomed flask equipped with a magnetic stirrer, a condenser, and a nitrogen inlet, 4-bromodiphenylether (50.1 g, 201 mmol), freshly distilled 2-methyl-3-butyn-2-ol (64.3 g, 892 mmol), copper(I) iodide (0.11 g, 0.60 mmol), triphenylphosphine (0.33 g, 1.3 mmol), and bis(triphenylphosphine)palladium(II) chloride (1.12 g, 1.6 mmol) were placed. The solids were carefully washed in with triethylamine (500 mL). The mixture was heated under reflux for 24 h. After the reaction mixture had been allowed to cool to room temperature, the solution was filtered through silica gel. The filtrate was poured into 5% hydrochloric acid solution and diluted with methylene chloride. After separation from the aqueous phase, the organic phase was subjected to purification via a silica-gel column chromatography with methylene chloride/hexane elution to give 40.5 g (80% yield) of light yellow oil. Anal. Calcd. for $C_{17}H_{16}O_2$: C, 80.93%; H, 6.39%; O, 12.68%. Found: C, 80.88%; H, 6.43%; O, 12.89%. Mass spectrum (m/e): 252 ($M^+$, 100% relative abundance).

EXAMPLE 2

(4-Phenyloxyphenyl)ethyne

Into a 1 L three-necked, round-bottomed flask equipped with a magnetic stirrer, a condenser, and a nitrogen inlet, 1-(2-methyl-3-butyn-2-ol)-2-(4-phenyloxyphenyl)ethyne (40.0 g, 159 mmol) was dissolved in toluene (700 mL). A solution of potassium hydroxide (2.2 g, 39.2 mmol) in methanol (40 mL) was added. The mixture was heated under reflux 14 h. The solution was concentrated to approximately 100 mL and then purified by silica-gel column chromatography with pentane elution to give 28.0 g (90% yield) of light yellow oil. Anal. Calcd. for $C_{14}H_{10}O$: C, 86.57%; H, 5.19%; O, 8.24%. Found: C, 86.52%; H, 5.25%; O, 8.29%. Mass spectrum (m/e): 194 ($M^+$, 100% relative abundance).

EXAMPLE 3

1,2-Bis(4-phenyloxyphenyl)ethyne

Into a 1 L three-necked round-bottomed flask equipped with a magnetic stirrer, a condenser, and a nitrogen inlet, (4-phenyloxyphenyl)ethyne (28.0 g, 144 mmol), 4-bromodiphenylether (27.7 g, 151 mmol), copper(I) iodide (0.10 g, 0.53 mmol), triphenylphosphine (0.30 g, 1.1 mmol), and bis(triphenylphosphine)palladium(II) chloride (1.00 g, 1.4 mmol) were placed. The solids were carefully washed in with triethylamine (500 mL). The mixture was then heated under reflux for 24 h. After the reaction mixture had been allowed to cool to room temperature, the solution was filtered through silica gel. The filtrate was poured into 5% hydrochloric acid solution and diluted with methylene chloride. After separation from the aqueous phase, the organic phase was subjected to a silica-gel column chromatography with petroleum ether elution to remove the excess 4-bromodiphenylether and then methylene chloride/hexane (33/67, v/v) elution to give 42.3 g (81% yield) of white crystals. It was again recrystallized from toluene to give 32.1 g (62% yield) of white flakes, m.p. 173–174° C. Anal. Calcd. for $C_{26}H_{18}O_2$: C, 86.17%; H, 5.01%; O, 8.83%. Found: C, 86.13%; H, 5.40%; O, 8.43%. FT-IR (KBr, $cm^{-1}$): 738, 3039, 3061. Mass spectrum (m/e): 362 ($M^+$, 100% relative abundance). $^1H$ NMR (DMSO-$d_6$, ppm) δ 6.97–7.00 (dd, 4H, Ar), 7.04–7.08 (m, 4H, Ar), 7.15–7.21 (t, 2H, Ar), 7.38–7.44 (t, 4H, Ar), 7.49–7.52 (d, 4H, Ar).

EXAMPLE 4

1,2-Bis(4-phenyloxyphenyl)benzil (Method 1) Into a 1 L three-necked round-bottomed flask equipped with a magnetic stirrer, a condenser, a dropping funnel and a nitrogen inlet, 1,2-bis(4-phenyloxyphenyl) ethyne (4.0 g, 11.0 mmol) and methyltrialkyl ammonium chlorides (Adogen 454, 1.25 g) were dissolved in methylene chloride (200 mL). A solution of potassium permanganate (16.0 g, 101 mmol) in acetic acid (30 mL) and water (500 mL) was slowly added through a dropping funnel. The mixture was gently heated under reflux for 10 h. After cooling down to room temperature, the mixture was poured in large flask, potassium bisulfate was added until the mixture became clear, and then a small amount of sodium bicarbonate was added. The organic layer was then separated, dried over magnesium sulfate, filtered, and solvent was removed under the reduced pressure to give 4.22 g of light yellow solid, which was re-dissolved in hot ethanol or heptane and allowed to cool to room temperature to give 3.88 g (89% yield) of light yellow powder, m.p. 119–120° C. Anal. Calcd. for $C_{26}H_{18}O_4$: C, 79.17%; H, 4.60%. Found: C, 79.83%; H, 4.89%. FT-IR (KBr, $cm^{-1}$): 1667. Mass spectrum (m/e): 394 ($M^+$, 100% relative abundance). $^1H$ NMR (DMSO-$d_6$, ppm) δ 7.00–7.06 (dd, 4H, Ar), 7.06–7.11 (m, 4H, Ar), 7.20–7.25 (t, 2H, Ar), 7.37–7.44 (t, 4H, Ar), 7.78–7.96 (dd, 4H, Ar). $^{13}C$ NMR (DMSO-$d_6$, ppm) δ 117.44, 120.46, 125.06, 127.51, 130.16, 132.20, 154.84, 155.89, 162.35, 163.56.

(Method 2). Into a 250 mL three-necked, round-bottomed flask equipped with a magnetic stirrer, a condenser, a dropping funnel and a nitrogen inlet, phenol (8.0 g, 85.0 mmol) and potassium carbonate (13.5 g, 98 mmol) were dispersed in NMP (100 mL). Then, the mixture was heated at 150° C. overnight. After the reaction mixture had been allowed to cool to 130° C., a solution of 4,4'-difluorobenzil (10.0 g, 40.6 mmol) in NMP (50 mL) was slowly added through the dropping funnel. The mixture was heated at 145° C. for 10 h. Upon cooling down to room temperature, the mixture was filtered and the filtrate was poured into 5% hydrochloric acid. The resulting precipitate was collected, air-dried, and dissolved in hot ethanol or heptane and allowed to cool to room temperature to give 13.6 g (85% yield) of light yellow powder: m.p. 120–122° C. Anal. Calcd. for $C_{26}H_{18}O_4$: C, 79.17%; H, 4.60%. Found: C, 79.19%; H, 4.75%. FT-IR (KBr, $cm^{-1}$): 1666. Mass spectrum (m/e): 394 ($M^+$, 100% relative abundance). $^1H$ NMR (DMSO-$d_6$, ppm) δ 7.01–7.05 (dd, 4H, Ar), 7.05–7.10 (m, 4H, Ar), 7.19–7.26 (t, 2H, Ar), 7.36–7.44 (t, 4H, Ar), 7.78–7.95 (dd, 4H, Ar). $^{13}C$ NMR (DMSO-$d_6$, ppm) δ 117.43, 120.45, 125.06, 127.50, 130.15, 132.20, 154.83, 155.88, 162.33, 163.55.

EXAMPLE 5

2,3-Bis(4-phenyloxyphenyl)-6-quinoxaline-carboxylic acid

Into a 250 mL three-necked, round-bottomed flask equipped with a magnetic stirrer, a condenser, and a nitrogen inlet, 3,4-diaminobenzoic acid (2.65 g, 17.4 mmol) was dissolved in acetic acid (150 mL). 4,4'-Diphenyloxybenzil (6.55 g, 16.6 mmol) was then added and heated under reflux for 12 h. Upon cooling to room temperature, the resulting dark red solution was filtered and the filtrate was poured into 5% hydrochloric acid. The resulting light yellow precipitate was collected by suction filtration and air-dried. It was recrystallized from ethanol to give 7.0 g (83% yield) of bright yellow powder: m.p. 224–226° C. Anal. Calcd. for $C_{33}H_{22}N_2O_4$: C, 77.63%; H, 4.34%; N, 5.49%; O, 12.54%. Found: C, 77.71%; H, 4.39%; N, 5.27%; O, 12.41%: FT-IR (KBr, $cm^{-1}$): 1242, 1488, 1588, 1697. Mass spectrum (m/e): 510 ($M^+$, 100% relative abundance). $^1H$ NMR (DMSO-$d_6$, ppm) δ 6.99–7.02 (d, 4H, Ar), 7.06–7.09 (d, 4H, Ar), 7.14–7.25 (m, 2H, Ar), 7.39–7.45 (t, 4H, Ar), 7.52–7.55 (d, 4H, Ar), 8.14–8.17 (d, 1H, Ar), 8.26–8.29 (dd, 1H, Ar), 8.61–8.62 (d, 1H, Ar). $^{13}C$ NMR (DMSO-$d_6$, ppm) δ 117.00, 117.66, 119.08, 119.91, 123.91, 129.01, 129.99, 130.08, 130.25, 131.57, 131.66, 131.83, 132.03, 133.13, 139.52, 142.17, 153.23, 153.83, 154.93, 155.79, 155.85, 157.55, 157.66, 160.69, 166.53.

Having thus described exemplary embodiments of the present invention, it should be noted by those skilled in the art that the disclosures herein are exemplary only and that alternatives, adaptations and modifications may be made within the scope of the present invention.

We claim:
1. 2,3-bis(4-phenyloxyphenyl)-6-quinoxaline carboxylic acid.

* * * * *